United States Patent [19]

Elloy et al.

[11] Patent Number: 4,904,269
[45] Date of Patent: Feb. 27, 1990

[54] HIP JOINT PROSTHESIS

[75] Inventors: Martin Elloy, Fenton, England; Paulo Gallinaro, Via Governolo 28, 10128 Turin; Giacomo Masse, Via Sant-andrea 20, 12038 Savigliano (Cn), both of Italy

[73] Assignees: Paulo Gallinaro, Turin; Giacomo Masse, Savigliano, both of Italy

[21] Appl. No.: 361,666

[22] Filed: May 30, 1989

Related U.S. Application Data

[63] Continuation of Ser. No. 112,679, Oct. 23, 1987, abandoned.

[30] Foreign Application Priority Data

Oct. 25, 1986 [GB] United Kingdom ................. 8625603
Aug. 26, 1987 [GB] United Kingdom ................. 8720084

[51] Int. Cl.$^4$ ............................................. A61F 2/32
[52] U.S. Cl. .......................................... 623/23; 623/18
[58] Field of Search ..................... 623/16, 18, 19, 20, 623/21, 22, 23

[56] References Cited

U.S. PATENT DOCUMENTS 4,681,590 7/1987 Tansey ................................. 623/23
4,718,915 1/1988 Epinette ............................... 623/23

FOREIGN PATENT DOCUMENTS 508686 1/1955 Canada ................................. 623/23
2247560 10/1973 Fed. Rep. of Germany ........ 623/23
2549717 2/1985 France ................................. 623/23

Primary Examiner—Richard J. Apley
Assistant Examiner—David J. Isabella
Attorney, Agent, or Firm—Darby & Darby

[57] ABSTRACT

A hip prosthesis having a stem (1) for introduction into the medullary cavity of a femur (13) and a head (2) which replaces a natural femoral head is characterized in that a plate-like anchoring member (3) is movably mounted at or near to the proximal end. The anchoring member is movable from an inoperative position in which it is housed within the general confines of the stem for the purpose of introducing the stem into the medullary cavity, to an operative position in which the member projects laterally of the stem to engage and anchor itself in adjacent cancellous bone.

10 Claims, 3 Drawing Sheets

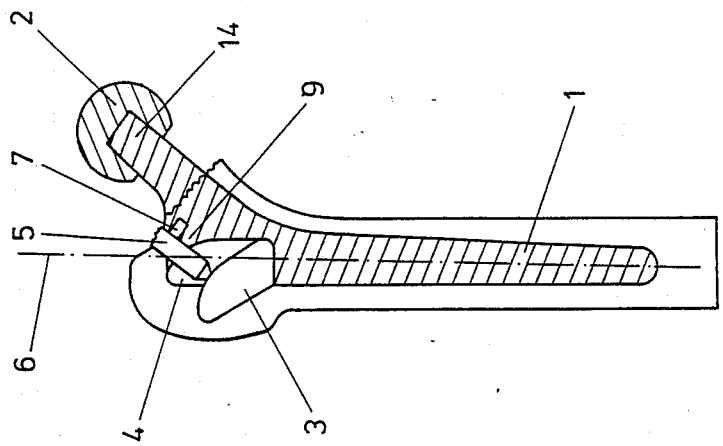
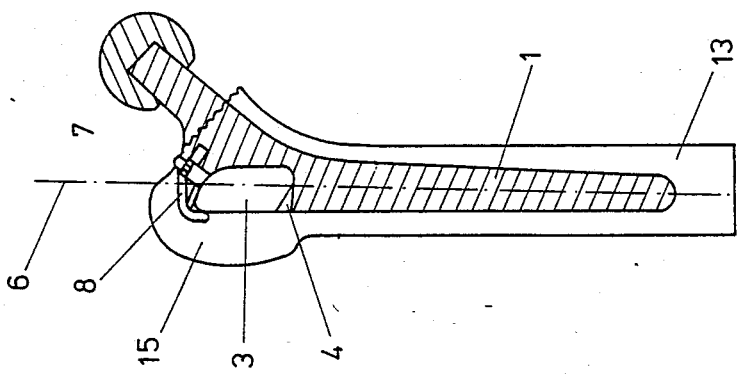
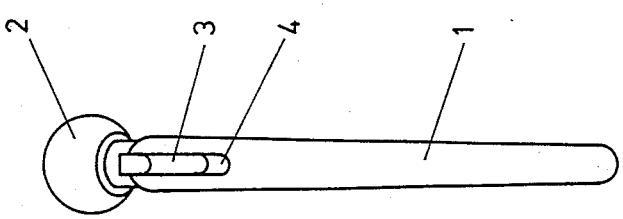

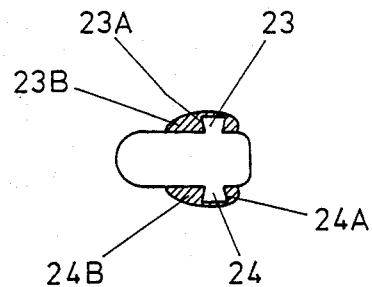
FIG. 7
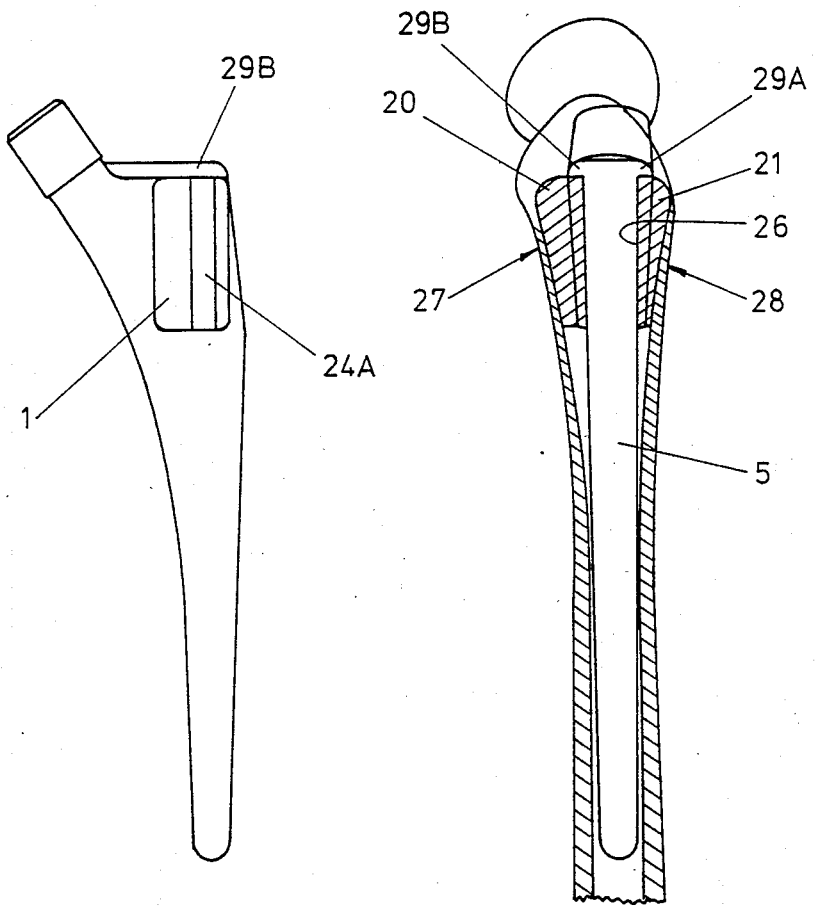
FIG. 5
FIG. 6

HIP JOINT PROSTHESIS

This is a continuation of co-pending application Ser. No. 07/112,679 filed on Oct. 23, 1987, now abandoned.

This invention relates to a hip joint prosthesis which comprises a stem for insertion in a medullary cavity of a femur, and a head for replacing a natural femoral head.

Treatment of hip arthrosis by joint replacement is usually achieved by relining the acetabulum with a plastics socket and replacing the natural femoral head with a metal prosthesis. The latter is usually fixed to the bone by means of a stem which extends down the natural medullary cavity of the shaft.

Such stems can be fixed to the bone with or without the use of a grouting medium or bone cement. In the former case bone is cleared from the medullary cavity to produce a space larger than that required to accommodate the stem, taking care to remove any poor quality bone which has inadequate strength to support the natural loads transmitted through the prosthesis. A grouting medium is then inserted into the cavity to fill the gap between implant and bone and thereby provide means for loads to be transmitted from the implant into the remaining bone.

The advantage of such a method is that accurate bone resection is not required and natural or surgically produced bone defects can be filled with bone cement. In this way immediate mechanical fixation can be achieved leading to early weight bearing and rehabilitation of the patient.

The disadvantages of such a method result from the inherent weakness of the cement which is exacerbated by poor distribution and/or contamination by blood during surgery.

Implants of this sort are sometimes fitted without the use of a grouting medium, in which case accurate bone resection is attempted and the prosthesis carefully selected to give the tightest possible fit into the cavity produced so as to provide a mechanically stable support against physiological loading.

Sometimes the surface of the implant is treated to provide a porous or roughened structure into which it is intended that bone or other tissue will grow to key the implant to the bone.

The advantage of such a system is that no cement is used, thus eliminating its long term inherent weakness and the short term toxic effects.

The disadvantages are:

Firstly, accurate bone resection to suit available implants is difficult and often impossible to achieve, such that some initial looseness or lack of support exists. In such cases the implant will migrate to a more stable position, which may not be an ideal orientation for durable service. Looseness can, and often does, result in oscillating movements with progressive increase in looseness.

Secondly, surface treatments required for tissue ingrowth may act as notches and stress raisers causing significantly increased risk of failure due to fatigue fracture of the implant.

Even so, such surface conditions require a considerable time before tissue ingrowth and stabilisation of the implant occurs. This results in significant detriment to early patient rehabilitation.

Surface treatment may also result in a considerable increase in the surface area of the implant, such that any diffusion of metal ions is increased with additional risk to toxic or pathological effects on surrounding and even remote tissues.

Because the spongiosa bone in the proximal femur is relatively weak and the implant cross-section is limited by physical access during insertion, it follows that good proximal support for cementless implants is difficult to achieve.

The present invention has been developed primarily with a view to provide a hip joint prosthesis which can be implanted without the necessity for a grouting medium or bone cement to be used, and yet in a more secure and reliable manner than hitherto possible.

The invention has proceeded from a recognition that improved support of a cementless implant could be achieved by resting the implant on the calcar femoral (the main load bearing structure in the proximal femur) and by providing the widest possible profile when viewed in the anterior to posterior (A/P) direction.

According to the invention there is provided a hip joint prosthesis which comprises a stem having a distal end for introduction into a medullary cavity of a femur and a proximal end, and a head connected to the proximal end of the stem and serving to replace a natural femoral head, in which a plate-like anchoring member is movably mounted at or near to the proximal end of the stem for movement from an inoperative position in which it is housed substantially within the general confines of the stem, for the purpose of introduction of the stem into the medullary cavity, and to an operative position in which the plate-like member projects laterally from the stem so as to engage and to anchor itself in adjacent cancellous bone of the trochanter, and means is provided, on or in the proximal end of the stem, for driving engagement with, or to permit a driving device to engage with the anchoring member in order to displace the latter to its operative position.

Said means may comprise a hole or passage formed in the proximal end of the stem, and through which can extend a driving member to engage with a surface portion of the plate-like member. The driving member may comprise a screw, in which case the hole or passage is formed with a complementary internal thread.

In use of the hip joint prosthesis according to the invention, the plate-like anchoring member forms a fin, blade or wing which can penetrate the cancellous bone of the trochanter by a crushing action, rather than a cutting action. The force required to do this is opposed by the the calcar femoral which acts as a pivot, causing the stem to tip in a varus direction, until stopped by firm contact between the distal stem and the lateral cortex of the bone shaft. Thus, at the time of surgery, the implant is forced into its most stable position, and locked there by the forces of contact with the bone.

In addition, the "blade" form of the anchoring member provides a large A/P profile, and lies within a size track in the cancellous bone of the trochanter. Therefore, it provides excellent anti-rotation stability for the implants. This is an important advantage of the hip joint prosthesis, since the application of twisting to prostheses in the medullary canal is a major contributor to stem fractures with existing prosthesis in patients where good proximal prosthetic support has not been achieved.

The mounting provided on or in the proximal end of the stem for the anchoring member may take any convenient form, to permit a generally pivotal movement of the anchoring member to its operative position, and it is preferred that the arrangement should be simple in nature, though sufficiently robust to withstand the reaction forces generated during the movement of the anchoring member into the cancellous bone.

Preferably, the mounting comprises a slot formed in the stem, which extends parallel to the general longitudinal extent of the stem and radially inwardly by a sufficient extent to allow the plate-like member to be housed therein i.e. without projecting laterally from the stem, when in the inoperative position. To prevent premature displacement of the anchoring member to its operative position, a keeper may be mounted temporarily on the proximal end of the stem to retain the member in the inoperative position.

The movable anchoring member described above serves, when in its operative position, to prevent subsidence of the prosthesis and also protects it against medial or lateral movements, as well as resisting torsion because of its wide and asymmetric anterior-posterior profile. It does not however provide direct support for the prosthesis anteriorly and posteriorly.

The prosthesis according to the invention is therefore preferably provided, in addition to the movable anchoring member, with at least one wedge for insertion between the stem of the prosthesis and the femur at or close to the proximal end, said wedge having a stem engaging surface which, in use, locates the wedge on the stem and a bone engaging surface which, in use, engages the cortical bone of the femur on the anterior or posterior side.

Preferably two such wedges are employed, one for insertion between the stem and the femur on the anterior side and the other for insertion on the posterior side. With two wedges and the movable anchoring member, the prosthesis is supported in both the medio-lateral and anterior-posterior directions.

The wedges conveniently take the form of a solid element having a bone-engaging surface which tapers towards the distal end, so that when inserted the wedges are forced against the flared inner profile of the cortical bone of the femur, thus transmitting some of the downward forces on the prosthesis onto the anterior and posterior cortexes.

In a preferred arrangement the stem engaging surface of each wedge includes a longitudinally running groove, and the stem of the prosthesis includes, on both the anterior and posterior sides, a longitudinally running rib which mates with said groove to locate the wedge onto the stem.

The ribs on the stem themselves taper towards the distal end so as to provide a wedge-like appearance in the medio-lateral direction which is sufficient in some cases to support the prosthesis anteriorly and/or posteriorly without the use of the wedges.

It is important that the wedges are prevented from moving upwardly on the stem, and therefore the stem is provided, proximally of the ribs, with shoulders which serves as a stop to limit upward movement of the wedges as the prosthesis is inserted into the medullary cavity of the femur.

Preferably, a number of wedges of differing size and shape are provided, which, together with a choice of different stem sizes, allows the surgeon to build up a custom-made prosthesis which is effectively supported on all load bearing structures of the proximal femur, and the problems of achieving good proximal support for a cementless implant are eliminated. Left/right assymmetry is produced simply by fitting the appropriate wedges on one side or the other of the plane of symmetry.

Embodiments of hip joint prosthesis according to the invention will now be described in detail, by way of example only, with reference to the accompanying drawings, in which:

FIG. 1 is substantially a side view of a first embodiment;

FIG. 2 is substantially a front view of the first embodiment, and in which an anchoring member is housed within the confines of the stem of the prosthesis in an inoperative position;

FIG. 3 is a view, similar to FIG. 2, but showing the anchoring member displaced to an operative position.

FIG. 5 is substantially a front view of yet another embodiment of hip joint prosthesis, FIG. 6 is substantially a side view of the embodiment shown in FIG. 5, in combination with two wedges and implanted in the femur, and FIG. 7 is a plan view from above of the prosthesis shown in FIG. 5.

Figure 4:
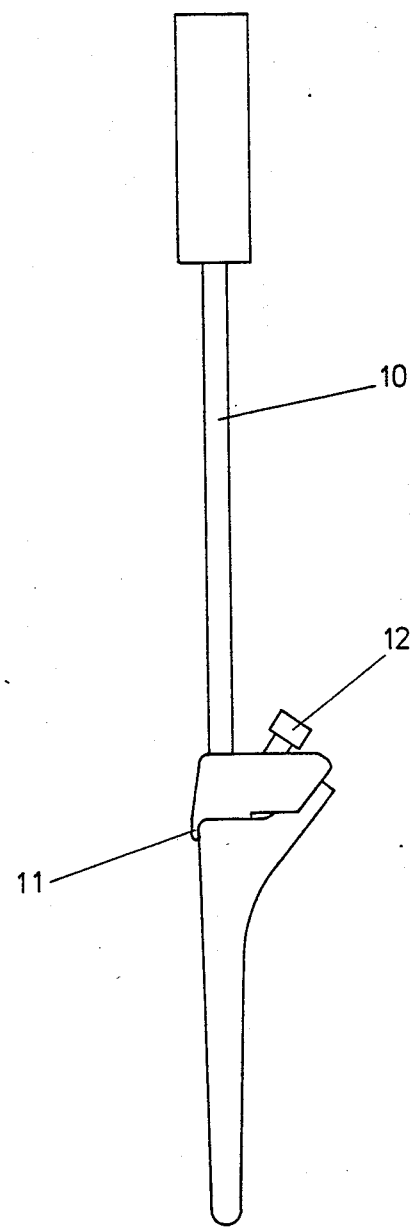
FIG. 4 is a view, similar to FIG. 2, of a further embodiment of hip joint prosthesis in combination with an introducing instrument.

Referring now to the drawings, there will be described a hip joint prosthesis having improved resistance to twisting of the prosthesis in the medullary canal of a femur, and without the use of a grouting medium or bone cement. As will become apparent from the subsequent detailed description, the hip joint prosthesis has a wider profile than hitherto achieved, and this is a significant advantage, having regard to the physiological loads which tend to drive implant stems into varus, and at the same time twist in an oscillating fashion during activity. Such movements are best resisted by resting the stem on the calcar femoral or medial cortex, and allowing the distal stem to press against the lateral cortex of the shaft of the femur.

In FIGS. 1 to 3, there is shown a hip joint prosthesis having a stem 1 which is of suitable proportions such that it provides the best practicable fit in a prepared medullary cavity of a femur 13. The stem 1 may be made of any implantable material of sufficient strength, but ideally should be of titanium alloy. The stem 1 has a distal end which is inserted with the medullary canal of the femur and rests within the confines of the substantially tubular portion of the femoral shaft, and also has a proximal end to which is connected a prosthetic head 2 for replacing a natural femoral head. The head 2 may be integral with the stem 1, or attached by a variety of suitable means. The head 2 may be made of a number of hard implant materials, such as ceramic, stainless steel, cobalt chrome alloy or treated titanium. However, the presently preferred material is a ceramic material.

In order to provide an enlarged A/P profile at the proximal end of the stem 1, and to improve the resistance to applied twisting forces, a plate-like anchoring member 3 is mounted at or near to the proximal end of the stem, and takes the form of a wing, fin or blade. The member 3 is mounted for movement from an inoperative position, as shown in FIG. 2, to an operative position as shown in FIG. 3. In the inoperative position, the member 3 is housed substantially within the general confines of the stem, for the purposes of introduction of the stem into the medullary cavity. In the operative position, the member 3 projects laterally of the stem so as to engage and to anchor itself in adjacent cancellous bone of the trochanter 15.

The mounting provided in the stem for the member 3 comprises an axially extending slot 4 in the lateral surface of the stem which extends medially by a sufficient extent to accommodate the member 3 when in its inoperative position. The member 3 is a good sliding fit within the slot 4, such that it is free to move laterally, though it is prevented from moving in an anterior or posterior direction. The lower end of the slot 4 may be perpendicular to the axis 6 of the stem, or inclined or notched medio-inferiorly so as to provide some limited constraint to lateral movement of the distal tip of the member 3 during deployment. The inferior (lower) edge of the member 3 is shaped to allow a generally pivotal movement about the tip within the slot 4 the latter portion of the stem 1 inherently acting as a fulcrum for the pivoting member.

To permit deployment of the anchoring member 3, when in situ within the femur 13, means is provided, on or in the proximal end of the stem 1, for driving engagement with, or to permit a driving device to engage with, the anchoring member in order to displace the latter to its operative position. In the embodiment shown in FIGS. 1 to 3, such means comprises an opening such as internally threaded hole or passage in which is received an elongate drive element such as a drive screw 5. Upon rotation of the screw 5, when the implant is fully in position, it engages a surface portion of the anchoring member 3 in order to force the proximal end thereof distally and laterally i.e. radially outwardly relative to the stem 1 utilizing a constructional arrangement which is in the nature of a second class lever (see FIG. 3). This action causes the member 3 to pivot about its distal tip and deploy from the slot 4 in the stem 1 and into the cancellous material of the trochanteric bone 15.

In order to prevent premature displacement of the anchoring member 3, a keeper may be provided which is mounted temporarily on the proximal end of the stem to retain the member 3 in its inoperative position. In the arrangement shown in FIG. 2, this takes the form of a keep plate 8 which locates in the threaded hole of the stem and wraps over the upper edge of the member 3. The keep plate 8 is ideally manufactured from a plastics material, which will not damage the metal implant surfaces and is sufficiently compliant to spring into position.

The screw 3 may be prevented from accidental movement by a pad of plastics material 7, which lies in a corresponding recess which intersects the tapped hole in the stem and interferes with the free passage of the screw thread. The screw 5 thus has to form a thread in the pad of material 7 as it winds itself inwardly. This produces a resistance to the screwing in or out of the screw.

It will be seen from FIGS. 2 and 3 that the head 2 is joined to the proximal end of the stem 1 via a neck 14. In an alternative arrangment, as shown in FIG. 4, the anchoring member 3 may be retained in its inoperative position by means of an introducing instrument 10, by which the prosthetic hip joint is inserted into the medullary cavity of the femur 13. This provides an alternative means for retaining the anchoring member captive in its inoperative position, in that a flange 11 is provided on the instrument 10, which projects over the upper edge of the anchoring member 3 to retain it in the inoperative (retracted or recessed) position during insertion. The instrument 10 is located on the taper section of the neck 14, and is secured by means of a screw 12 entering tapped hole 9.

FIGS. 5 to 7 illustrate another embodiment of the prosthesis in which additional support is provided anteriorly and posteriorly by wedges 20,21 for location on the stem by means of longitudinally running, outwardly protruding or raised, ribs 23,24 on the stem which mate with corresponding longitudinally running grooves 23A,24A on the stem-engaging surfaces 25,26 of the wedges. The grooves and ribs are both "dovetail" shaped, to secure positive mating engagement.

The wedges taper towards the distal end so that when they are fitted on to the stem from the distal end and the stem inserted into the medullary cavity of the femur, the bone engaging surfaces 23B and 24B of the wedges are forced against the anterior and posterior cortexes, 27,28 of the proximal femoral bone.

Shoulders 29A,29B on the stem immediately above the ribs 23A,24A act as stops to prevent upward movement of the wedges on the stem as the prosthesis is inserted into the femur.

The ribs 23,24 on the stem are themselves tapered towards the distal end, so as to present a wedge appearance which is alone sufficient, in some cases to fill the space between the stem and the bone on the anterior/posterior sides.

The wedges 20,21 are provided in a variety of different shapes and sizes to suit the requirements of different patients, the surgeon choosing the most suitable pair of wedges at the time of implantation.

To implant the prosthesis shown in FIGS. 5 to 7, the following procedure is adopted:

1. A taper pin reamer is used to prepare the distal femur.
2. A broach/trial stem is used to prepare the proximal femur.

Incremental sizes of both above are provided and the larger broach/trial is left in position as a trial prosthesis.

3. The trial/broach is the same shape as the final prosthesis except is lacks the superior wedge support shoulders. In other words, the ribs continue to the top of the stem.
4. Wedge broaches mounted on a suitable handle and in the same range of sizes as the wedge implants, can be driven down over the ribs on the trial stem to remove the cancellous bone and create cavities to accept suitable implant wedges.
5. When the optimum selection of stem and wedge sizes have been determined an actual prosthesis can be assembled to this pattern at the operating table and inserted.
6. Finally, the movable anchoring element (omitted from FIGS. 5 to 7 for the sake of clarity), as described above can be deployed.

In another method, the trial/stem can have shoulders, as on the prosthesis, and wedge broaching is achieved by removing the trial stem, fitting appropriate wedge broaches to it and rebroaching the femur within the assembly.

In either method, the final trial/broach can be used with a suitable head unit attached to carry out a trial reduction of the joint before implanting the actual prosthesis.

The disclosed embodiments of hip joint prosthesis provide for secure implantation, and substantial resistance to applied torsional forces. Further, the deployment of the anchoring member is achieved in a reliable and robust manner. In the event of subsequent removal of the implant being required, it is presently contemplated that this may be achieved by drilling through the trochanteric bone 15 to permit engagement of a suitable tool with the anchoring member 3 in order to displace the latter back into its housed position.

We claim:

1. A hip prosthesis comprising a stem having a distal end for introduction into a medullary cavity of a femur and a proximal end, a head connected to the proximal end at a first point on the stem in a direction generally perpendicular to the anterior/posterior plane of the stem, and serving to replace a natural femoral head, said stem having a slot formed therein at the proximal end thereof at a second point generally diametrically opposite said first point;

an anchoring plate, said plate being substantially flat and broad and dimensioned to be movably mounted in said slot; and positioning means formed in the stem adjacent the proximal end and operatively connected to said slot, whereby said plate may be moved from an inoperative position, a position where the plate is housed in the slot substantially within the general confines of the stem for introducing the stem into the medullary cavity, to an operative position by coupling a positioning drive means to said positioning means thereby operatively displacing the plate generally radially in a unidirectional outward operative position in which it projects laterally from the stem to engage and anchor itself in an adjacent cancellous bone of the trochanter.

2. The prosthesis of claim 1 wherein the prosthesis further comprises drive means and wherein the positioning means include an opening formed in the proximal end of the stem and the drive means include an elongate drive element operatively extending through the opening for engaging a surface portion of the anchoring plate.

3. The prosthesis of claim 2 wherein the drive element has screw threads thereon and the opening is formed with a complementary internal thread provided for engagement with the screw threads on the drive element and the anchoring plate is positioned as a function of the degree of extension of the drive element through the opening.

4. The prosthesis of claim 1 wherein the slot is defined by a blind bore structure which extends generally parallel to the longitudinal axis of the stem and radially inwardly by a sufficient extent to allow the anchoring plate to be housed therein completely with in the adjacent confines of the stem and without projecting laterally from the stem when in its inoperative position.

5. The prosthesis of claim 1 further including keeper means removeably mounted on the proximal end of the stem and having a retention portion arranged to retain the anchoring plate in its inoperative position.

6. The prosthesis of claim 1 further including at least one wedge arranged for insertion between the stem and the femur adjacent the proximal end thereof, the wedge having a stem engaging surface which locates the wedge on the stem and a bone engaging surface which engages the cortical bone of the femur on the anterior or posterior side.

7. The prosthesis of claim 6 wherein two wedges are provided and wherein one wedge is disposed on the anterior surface of the stem and the other wedge is disposed on the posterior surface of the stem.

8. The prosthesis of claim 6 wherein each wedge is in the form of a solid wedge element having a bone engaging surface which tapers toward the distal end of the stem.

9. The prosthesis of claim 6 wherein the stem engaging surface of each wedge includes a longitudinally running groove and the stem of the prosthesis includes, on both the anterior and posterior sides, a longitudinally running outwardly protruding rib which mates with the groove to locate the wedge on the stem.

10. The prosthesis of claim 6 wherein the stem is provided with shoulder means for serving as a stop to limit the upward movement of each wedge as the prosthesis is inserted into the medullary cavity of the femur.

* * * * *

UNITED STATES PATENT AND TRADEMARK OFFICE
CERTIFICATE OF CORRECTION

PATENT NO. : 4,904,269

DATED : February 27, 1990

INVENTOR(S) : Martin Elloy, et al.

It is certified that error appears in the above-identified patent and that said Letters Patent is hereby corrected as shown below:

On the title page, item [75] should read --Paolo Gallinaro--.

Signed and Sealed this

Ninth Day of April, 1991

*Attest:*

HARRY F. MANBECK, JR.

*Attesting Officer*  *Commissioner of Patents and Trademarks*